United States Patent [19]

Courty et al.

[11] Patent Number: 4,659,742

[45] Date of Patent: Apr. 21, 1987

[54] PROCESS FOR MANUFACTURING A MIXTURE OF METHANOL AND HIGHER ALCOHOLS FROM SYNTHESIS GAS

[75] Inventors: Philippe Courty, Houilles; Daniel Durand, Rueil Malmaison; André Sugier, Rueil Malmaison; Edouard Freund, Rueil Malmaison, all of France

[73] Assignee: Institut Francais du Petrol, Rueil-Malmaison, France

[21] Appl. No.: 750,240

[22] Filed: Jul. 1, 1985

Related U.S. Application Data

[63] Continuation of Ser. No. 478,764, Mar. 25, 1983, abandoned.

[30] Foreign Application Priority Data

Mar. 26, 1982 [FR] France ................................ 82 05368

[51] Int. Cl.[4] .............................................. C07C 27/06
[52] U.S. Cl. ..................................... 518/713; 518/700; 518/714; 502/331; 502/328
[58] Field of Search ........................ 518/700, 713, 714

[56] References Cited

U.S. PATENT DOCUMENTS

| | | | |
|---|---|---|---|
| 4,122,110 | 10/1978 | Sugier et al. | 518/713 |
| 4,291,126 | 9/1981 | Sugier et al. | 518/713 |
| 4,346,179 | 8/1982 | Sugier et al. | 518/713 |
| 4,477,594 | 10/1984 | Greene et al. | 518/713 |

Primary Examiner—Howard T. Mars
Attorney, Agent, or Firm—Millen & White

[57] ABSTRACT

Process for manufacturing a mixture of methanol and higher alcohols by reacting carbon oxides with hydrogen in the presence of a catalyst containing simultaneously copper, cobalt, aluminum and at least one alkali or alkaline-earth metal A selected from lithium, sodium, potassium, rubidium, caesium, beryllium, magnesium, calcium, strontium and barium, in respective atomic ratios of Cu/Co=0.1–5, Al/co=0.7–4, A metals/Co=0.05–3.5, the proportion by weight of each metal to the total metals weight being respectively: copper: 10–65%, cobalt: 5–50%, aluminum: 5–40%, metal A: 0.1–15%, the homogeneity of the catalyst being such that the atomic ratio cobalt/aluminum does not vary by more than 15% with respect to its average value, on a scale of 5 nanometers.

17 Claims, No Drawings

PROCESS FOR MANUFACTURING A MIXTURE OF METHANOL AND HIGHER ALCOHOLS FROM SYNTHESIS GAS

This application is a continuation of application Ser. No. 478,764, filed Mar. 25, 1983, abandoned.

BACKGROUND OF THE INVENTION

This invention concerns a catalytic process for manufacturing a mixture of methanol and higher alcohols by reaction of carbon monoxide with hydrogen. The obtained alcohols are mainly saturated primary alcohols.

French Pat. Nos. 2 369 234 and 2 444 654 describe the use of catalysts suitable for operating a process of manufacture of an alcohol mixture from CO, $H_2$ or CO, $CO_2$, $H_2$ mixtures. These catalysts have generally a good selectivity in the conversion of carbon oxides and hydrogen to alcohols, and their selectivity to $C_2$ and higher saturated linear primary alcohols is often higher than 70% by weight. Finally their initial yield is high, in most cases amounting to 0.1 Ton of alcohols per ton of catalyst or more.

The obtained alcohols have numerous possibilities of use; in particular the production of a substantial proportion of $C_2$–$C_6$ alcohols is of interest when the considered use is to form, in admixture with hydrocarbon cuts, mixed hydrocarbon alcohols motor fuels. The higher alcohols are more compatible than methanol with the hydrocarbons and also facilitate the incorporation of methanol to the hydrocarbons.

SUMMARY OF THE INVENTION

It has now been found that a mixture of alcohols can be obtained by making use of catalysts of improved stability and having particularly long life times. The catalysts used according to the invention essentially contain copper, cobalt, aluminum, and at least one alkali and/or alkaline-earth metal (A) selected from the group formed of Li, Na, K, Rb, Cs, Be, Mg, Ca, Sr and Ba.

DETAILED DISCUSSION

Preferred alkali and/or alkaline-earth metals are Na, K, Rb, Ca and/or Ba.

The catalyst may optionally further contain zinc; it may also optionally contain a metal M selected from the group formed of manganese, iron, vanadium and rhenium. It may also optionally contain at least one metal N selected from the group formed of scandium, yttrium, thorium, zirconium and rare earth metals of atomic number from 57 to 71 included, as well as optionally chromium in low proportion.

These different metals are in the following proportions (in % by weight of metal with respect to the total weight of the metals):
Copper from 10 to 65% and preferably from 20 to 50%
Cobalt from 5 to 50% and preferably from 9 to 40%
Aluminum from 5 to 40% and preferably from 7 to 30%
Metal A from 0.1 to 15% and preferably from 0.2 to 10%

In addition, inside the above-mentioned range of composition by weight, it is necessary that the following atomic relative proportions of the different metals be obtained:
Cu/Co=0.1 to 5 and preferably 0.5 to 4.5
Al/Co=0.7 to 4 and preferably 0.9 to 2.6, and
A metals/Co=0.05 to 3.5, preferably 0.05 to 1.5 or more, in particular 0.08 to 0.75.

The catalyst may optionally contain other metals (% by weight):
Zinc, from 1 to 50% and preferably from 5 to 40%,
M metals, from 0.1 to 10% and preferably from 0.5 to 7%,
Chromium, from 0.1 to 10% and preferably from 0.5 to 7%,
N metals, from 5 to 50% and preferably from 6 to 42%.

In this case the additional metals are conveniently in the following atomic proportions:
M metals/Al=0.001 to 0.3 and preferably 0.005 to 0.2
Zn/Co=0.1 to 2 and preferably 0.2 to 1.2
Chromium/Al=0.001 to 0.3 and preferably 0.005 to 0.2
N metals/Al=0.05 to 1.5 and preferably 0.08 to 1.

Again optionally the catalyst may further contain at least 0.02 to 0.8% by weight of a noble metal of the platinum family (group VIII) and more particularly palladium, rhodium and ruthenium.

In order to be simultaneously active and stable in the synthesis of higher alcohols, and selective in the conversion of CO and $CO_2$ to oxygenated compounds (the by-products whose formation must be reduced to the maximum extent are hydrocarbons) the catalysts according to the invention must essentially have a very homogeneous composition and the active metals thereof, particularly cobalt, must be evenly distributed in each elementary catalyst particle.

The best results, in terms of selectivity of the CO and $CO_2$ conversion to oxygenated compounds and particularly higher alcohols, are obtained with catalyst for which the variation of the atomic ratio cobalt/aluminum is lower than 15% and preferentially lower than 10% with respect to the average value of this ratio, at the scale of 50 Å (5 nanometers).

The homogeneity of the composition on a nanometer scale can be determined for example by X-ray spectrometry in a scanning transmission electronic microscope (STEM) equipped with an X-ray detector of the doped silicon type covering the required space zone (e.g. 1 to 20 keV for the compositions according to the invention). The operation is conducted as follows: a representative sample of the catalyst is crushed to a fine powder (e.g. of particle size lower than 10 $\mu$m), then deposited on an electronic microscopy grid, if necessary after having been suspended in an organic solvent, subsequently evaporated. The material of which the electronic microscopy grid is made must be so selected as to avoid casual problems of spectral interferences or parasitic signals (for this reason copper grids cannot be used).

Among the materials giving satisfactory results, nylon, beryllium and carbon are to be mentioned.

The microscope to be used must simultaneously give images with a high resolution (0.5 to 1 nm) in the scanning mode (STEM mode) and have a high sensitivity in the X-ray microanalysis mode. An apparatus of the trade such as the STEM Vacuum Generator HB 501 is perfectly convenient (limit sensitivity better than 1000 atoms of a given element) to determine the homogeneity scale of the catalyst.

After selection of the zone to be analyzed (typically 2 to 5 nm) several countings are simultaneously effected, over a period of 100–1000 s, leading to a sufficiently accurate counting statistic (accuracy better than 10%).

From the intensities measured on the various selected peaks corresponding to the various elements present in the sample it is possible to determine their relative concentrations and then their respective atomic ratios according to well-known techniques in the field of X-ray emission (see for example REED S. J. B., Electron microprobe Analysis, Cambridge University Press-1975), for each of the particles forming the sample.

The compared samples must all have the same thickness. The average values of the correction coefficients are the following:

| Correction coefficients (based on Co—$K_\alpha$ = 1) | | |
|---|---|---|
| Measurement on the line | Element | Coefficient |
| $K_\alpha$ | Cobalt | 1.00 |
| $K_\alpha$ | Copper | 1.10 |
| $K_\alpha$ | Aluminum | 5.35 |
| $K_\beta$ | Zinc | 5.15 |

These coefficients have been determined by the applicant from mixed oxides roasted at high temperature (CO $Al_2O_4$, Cu $Al_2O_4$, Zn $Al_2O_4$, $Cu_{0.5}$ $Zn_{0.5}$ $Al_2O_4$, $Co_{0.5}$ $Zn_{0.5}$ $Al_2O_4$, $Co_{0.5}$ $Cu_{0.5}$ $Al_2O_4$) forming the reference samples.

The atomic ratio Al/Co will be calculated, for example, as follows ($i_{K\alpha}$ Al and $i_{K\alpha}$ Co are the average raw intensities over several countings.

$$Al/Co = 5.35 \ i_{K\alpha} Al / i_{K\alpha} Co$$

In order to obtain homogeneous catalysts, it is essential to first prepare a solution (by definition, homogeneous) containing copper, cobalt, aluminum and optionally zinc, and/or optionally at least one metal M, and/or optionally chromium, and then to transform said solution by a complexing reaction or a reaction of co-precipitation to a solid substance, called the catalyst precursor and always having a highly homogeneous composition.

The metals Cu, Co, Al, as well as optionally M, N, Zn, Cr, are used as soluble compounds, preferably soluble in acid medium, although the amino complexes (soluble in ammonia medium) of copper, cobalt, chromium, zinc and some of the M and N metals, may also be used in addition to the alkaline and/or ammonia-containing coprecipitation reactant.

There will be used, for example, soluble oxides (e.g. $Re_2O_7$), hydroxides, carbonates, hydroxycarbonates soluble in acid medium [for example Cu $CO_3$—Cu$(OH)_2$, Co$(OH)_2$], nitrates, oxalates, tartrates, citrates, acetates, acetylacetonates, or still anionic combinations such as aluminate, chromate, bichromate, permanganate, oxalatoferrate, oxalatocobaltate, vanadate or perrhenate. The nitrates are the soluble salts used the more frequently.

The metal A may be added at any of the unitary steps of manufacture. For example it can be added to the starting solutions to which are then further added at least one complexing agent before drying and roasting; it is also possible to make use of a carbonate, a hydrogenocarbonate and/or a hydroxide of at least one metal A, to prepare the catalyst precursor by coprecipitation between the compound of metal A and a solution containing the other metals Cu, Co, Al and, optionally Zn and/or M and/or N and/or Cr and to keep in the coprecipitate a controlled amount of metal A by controlling the subsequent washings; but it is preferable, after coprecipitation and dealkalination by thorough washing, to mix the precipitate, as such or previously dried, with a controlled amount of solution of soluble salts of metal A; or alternatively to thermally activate the precipitates of metals Cu, Co, Al and optionally Zn and/or M and/or N and/or Cr and then to add by mixing as previously at least one alkali and/or alkaline-earth metal A.

For the preparation of these catalytic masses, it is essential to use preparation techniques leading to a product whose composition is as homogeneous as possible and avoiding the segregation of the different elements during the various unitary steps of the preparation.

Hereinafter are described preferred methods of preparation of homogeneous catalytic masses leading to homogeneous catalysts active and selective in the production of higher alcohols and resulting in the lowest possible formation of hydrocarbons. By these methods the desired homogeneity can be maintained during the steps of the preparation.

A preferred preparation method, already described in 1968 by the applicant in the French patents Fr No. 1 604 707 and Fr No. 2 045 612 consists of preparing a solution containing Cu, Co, Al metals, optionally with Zn and/or M and/or N and/or Cr, as well as optionally at least one metal A and then adding at least one compound adapted to the formation of complexes preferably selected from:

organic acids having two or more acid groups, for example oxalic, malonic, succinic or gluraric acid, hydroxy-acids, for example glycolic, lactic, malic, tartaric or preferably citric acid, amino acids, for example aminoacetic acid, alanine or leucine, alkanolamines, for example monoethanolamine, diethanolamine, triethanolamine in a proportion of about 0.5 to 2 $COO^-$ or $-NH_2$ gram-equivalents per metal gram equivalent.

The obtained solution is evaporated under vacuum (e.g. in a rotary evaporator) so as to obtain a solution having a viscosity of at least 1 Pa.S, which is then transferred to a stove operated under vacuum between about 60° and about 120° C. and dried to such an extent as to reduce the water content to less than 10% by weight. There is so obtained a transparent vitreous mass, homogeneous and amorphous in X-ray diffraction which is then thermally activated in nitrogen or in the presence of an oxygen-containing gas, for example between about 300° and about 600° C. for a sufficient time to reduce the volatile materials content of the oxide to less than 10% and preferably less than 6% by weight.

After thermal activation, a controlled amount of metal A can be optionally added to the activated product according to the operating process hereinafter described.

Another preferred mode of preparation consists of preparing, by at least one reaction of co-precipitation, a hydrated, homogeneous precursor containing Cu, Co, Al metals and optionally Zn and/or M and/or N and/or Cr; the co-precipitation reaction is effected by bringing together, under hereinafter defined operating conditions, a solution of soluble salts of metals Cu, Co, Al, optionally Zn and/or M and/or N and/or Cr, with a solution of sodium and/or potassium and/or ammonium carbonate and/or hydrogenocarbonate and/or hydroxide, so as to obtain a co-precipitate which, after subsequent washing, forms the homogeneous hydrated precursor.

All the techniques and apparatus described in the prior art may be used or applied for operating the process of the invention; for example the solution of Cu, Co, Al and other metal salts may be added to the alkaline solution or conversely. Preferably both solutions are simultaneously added, at flow rates regulated by the pH measured in the reaction zone, into a reactor provided with an efficient stirring system. A preferred operating manner consists of contacting the two solutions in a zone of maximum turbulence defined by the volume surrounding the stirring apparatus inside the reaction volume.

The average residence time, expressed in minutes and defined as the ratio of the total flow rate by volume (liters/minute) of the solutions introduced into the reactor to the reactor volume, expressed in liters, may range from 0.1 to 600 minutes, inasmuch as the reaction can be conducted either in a reactor operated continuously (called of stationary concentration and other conditions), whose useful volume may vary from a few cm$^3$ to about 10 liters, wherein the residence time varies from 0.1 to 15 minutes and wherefrom the reaction product is recovered in a continuous manner, (optionally matured in another reactor) then fed for example to a press filter or a rotary filter where it is washed, or in a batch-operated reactor where the residence time is at least 30 minutes and preferably at least 60 minutes, in which the reactants are continuously introduced, without simultaneously recovering the reaction product, and wherein the reaction product remains in the presence of the continuously introduced reactants. This type of reactor whose volume (taking into account the concentration specifications of the solutions used and of the catalyst amounts to be prepared) varies from about 1 liter to about 1000 liters or more, is operated at variable concentrations, the other operating conditions being constant during the precipitation itself. This reaction mode is better adapted to the preparation of crystallized compounds whereas the reactor operated in a continuous manner is better adapted to the preparation of compound amorphous in X-ray diffraction.

A preferred embodiment of the invention consists of reacting a solution of soluble salts of the metals Cu, Co, Al and optionally Zn and/or Cr and/or M and/or N, brought to a temperature from 0° C. to 30° C. and containing at least one gram atom of the assembly of metals (Cu+Co+Al+Zn+M+N+Cr) per liter with a solution, at a temperature from 0° to 30° C., of sodium and/or potassium and/or ammonium carbonate and/or hydrogen carbonate and/or hydroxide containing at least 2 gram-atoms of alkali cations and/or $NH_4^+$ ammonium per liter, the co-precipitation reaction being conducted between 0° and 30° C., the pH, measured in the reaction volume, being adjusted at 7±1 pH units and the residence time of the mixture (co-precipitate+mother liquors) in the reaction volume being not longer than five minutes.

There is so obtained a homogeneous hydrated mixed hydrocarbonate, amorphous in X-ray diffraction, giving by X-ray diffraction and goniometer record a "falt" diagram. This product is then washed so as to reduce its content of alkali metals or ammonium (expressed by weight with respect to the total weight of oxides) to 0.1–3% by weight.

Another preferred embodiment of the invention consists of reacting, at a temperature of at least 30° C. and preferably at least 50° C., a solution of soluble salts of Cu, Co, Al, optionally Zn and/or Cr and/or M and/or N metals, at a concentration of at most 1 gr. at. of metals per liter, with a solution of sodium and/or potassium and/or ammonium carbonate and/or hydrogen carbonate and/or hydroxide at a total concentration of at most 2 gr.at. (for example from 0.1 to 1 gr.at.) of alkali metals and/or $NH_4$ per liter, the coprecipitation reaction being conducted at a pH of 7±1 pH units, and the residence time in the reaction medium being at least 2 minutes; there is thus obtained a mixed hydrated hydroxy carbonate, homogeneous, at least partly crystallized in a rhombohedral structure.

This structure, which has been previously observed for other compositions, e.g. for pyroaurite which is a hydrated hydroxycarbonate of iron and magnesium (American Society for testing materials ASTM data sheet No. 25-521) may be indexed in a multiple hexagonal grid, of average parameters a=0.30–0.31 nm, c=2.24–2.25 nm and of hexagonal space group R-3M. The parameters may vary slightly in accordance with the composition of said hydrated mixed hydroxy carbonate.

By way of example, the indexation of the X-ray diffraction diagram of the hydrated crystallized precursor of catalyst No. A is given in Table I.

The crystallized compound may then be matured, for example, between 50° and 100° C. at atmospheric pressure or between 100° and 200° C. in an autoclave, under pressure, for 15 minutes to 5 hours, in the presence of its mother-liquors or of its washing waters. During this maturation step, a pH increase is generally observed, in most cases ,f at most 1.5 pH unit, with respect to the precipitation pH. It is observed that, unexpectedly, this maturation treatment improves the crystallinity and/or increases the size of the crystallites of the crystallized hydrated precursor.

The maturation step, when the precipitation is effected in "batch" may be conducted in the same reactor, after having discontinued the reactants introduction. It is also possible, in the case of continuous precipitation, to recover the obtained precipitate under stationary conditions (temperature, concentrations, pH, rate of introduction of the reactants) and to mature it, after optional washing, in another reactor or in an autoclave.

Preferably the crystallized mixed hydroxycarbonate is prepared at a reaction temperature of at least 50° C., with a concentration of the solution of salts of metals Cu, Co, Al (Zn) (Cr) (M) (N) from 0.1 to 0.6 gr.at. of metals per liter and a concentration of alkali metals and/or ammonium from 0.2 to 1.2 gr.at. per liter and with a reaction time of at least 5 minutes.

After precipitation and optional maturation in the mother-liquors, the crystallized precipitate is washed so as to reduce its alkali content (expressed by weight of alkaline substance with respect to the total weight of oxides) to 0.01–5% by weight and, preferably, to 0.05–0.5% by weight, and then optionally matured in the washing waters.

Another preferred embodiment consists of effecting a precipitation in two separate steps. In a first step, a solution containing at least two metals selected from the group of: aluminum, zinc, chromium, M metals, N metals, copper, is reacted with a basic solution containing the alkali metals and/or the ammonium ion, in the above-mentioned conditions, resulting in the formation either of an amorphous precipitate or of a crystallized precipitate, the suspension of the so-formed precipitate being reacted, for example, in a second reactor, with a solution containing cobalt and at least a part of aluminum, optionally with one or more metals selected from zinc, copper, chromium, M metals, N metals and a basic solution containing alkali metals and/or ammonium, the flow rates of these two solutions being regulated by the pH measured in the precipitation zone, and the flow rates by weight of the metals solution and of the suspension of preformed co-precipitate being themselves adjusted to each other so that the overall composition of the finally obtained mixed precipitate corresponds to the above-mentioned composition (copper, cobalt, aluminum, optionally with zinc, chromium and/or M and/or N) in the above stated atomic ratios. This method may be used particularly to obtain highly active and efficient catalysts.

The two co-precipitates can be either amorphous or crystallized or mixed (one amorphous, the other crystallized); the first co-precipitate can be amorphous or crystallized when added into the reaction in which the second co-precipitate is formed; similarly the second co-precipitate may be formed itself in the above-mentioned operating conditions leading either to an amorphous or to a crystallized product. The order of formation of the two precipitates may optionally be inverted.

After precipitation and washing, a homogeneous (crystallized or amorphous) hydrated precursor is obtained, which contains from about 10% to about 30% by weight of oxides when amorphous and from about 15% to about 60% by weight of oxides when crystallized.

In this amorphous or crystallized precursor, the metals distribution is very homogeneous and the atomic ratios Cu/Co, Al/Co and optionally Zn/Co and/or M/Co and/or N/Co (M and N being one of the M metals and/or one of the N metals) measured as above have relative variations of less than 15% and preferentially less than 10% on a 5 nm scale.

In the mixed precursors obtained by precipitation in two separate steps and formed by juxtaposition of homogeneous particles of sizes ranging from about 3 to about 100 nm, and of different compositions, the measurement of the aluminum/cobalt ratio is effected at high resolution on specified particles containing cobalt, aluminum (at least partly) and optionally zinc and/or chromium and/or at least one M metal and or at least one N metal.

The copper-containing particles are also homogeneous with respect to one another.

A first mode of adding one or more A metal(s) (at least one alkali or alkaline-earth metal) consists of contacting the precipitate with a solution containing the one or more A metal(s) and then stirring the mixture so that, after the precipitate has been suspended in the alkaline solution and then optionally filtered, it contains the above mentioned A metals in convenient proportion.

The drying of the precipitate suspension and of A metals in solution may be effected, for example by spray-drying. The alkalinized precipitate in then obtained as a normalized powder containing about 60 to about 85% by weight of oxides, either amorphous when obtained from an amorphous hydrated precursor, or crystallized when obtained from a crystallized product.

It is also possible to separate the precipitate from the alkalinizing medium by filtration and then to dry it in a stove, for example between about 20° and about 150° C., so as to reduce its oxides content to about 65–85% by weight.

The drying of amorphous hydrated precursors, either alkalinized or not alkalinized, is as such a process for manufacturing the crystallized hydrated precursor. As a matter of fact it has been observed that, unexpectedly, the initially amorphous precipitate crystallizes when dried at a temperature from about 40° to about 120° C. In order to maintain the amorphous hydrated precursor, alkalinized or not, in its initial amorphous state, it is preferable to effect an instantaneous drying, for example by spray-drying, e.g. at 150°–350° C. in less than 10 seconds. The obtained product then consists of cenospheres of 3–700 μm diameter and of homogeneous composition.

Another alkalinization mode consists of adding at least one metal A as an aqueous and/or organic solution which can be admixed with the dried precipitate (amorphous precipitate, dried by spray-drying, or crystallized precipitate). A homogeneous paste is obtained which is then dried according to any suitable technique.

After the homogeneous precipitate (amorphous or crystallized) has been obtained, washed, alkalinized (as wet precipitate or by addition to the dried precipitate) then subsequently dried, a homogeneous product, either amorphous or crystallized, containing Cu, Co, Al metals optionally with Zn and/or Cr and/or M and/or N together with at least one A metal, is obtained in the above mentioned proportions.

This precipitate is then thermally activated as stated below but this thermal activation treatment may also be effected on a precipitate thoroughly dealkalinized by washing (amorphous or crystallized) not yet containing at least one A metal and having the above stated homogeneity properties.

The thermal activation consists of treating the dried, alkalinized or not yet alkalinized, precipitate at a temperature from about 250° to about 750° C. and preferably from about 300° to about 600° C. for a sufficient time, for example at least 0.5 hour, in order to obtain a homogeneous activated catalyst containing at most 12% by weight of volatile substances (the proportion of volatile substances is measured, for example, by activation, in the presence of air, of a given weight of product, placed on a dish and roasted at 500°–600° C. for 4 hours).

The thermal activation may be conducted, according to the case, in the presence of an inert gas containing from 0 to 50% of oxygen, thereby obtaining a homogeneous mixed oxide whose atomic ratio Co/Al does not vary by more than 10% at the scale of 5 nm.

The thermal activation may also be conducted in a reducing medium (mixture of inert gas with reducing gas containing from 0.1 to 100% of reducing has); the reducing gases, used alone or as mixture are hydrogen and ammonia.

The thermal activation in a medium having, as a whole, a reducing action may be effected either on the dried precursor or on the mixed oxide, previously activated in an overall oxidizing medium.

After thermal activation in a medium which, as a whole, has a reducing effect, the mixed oxide may be partially reduced (by the hydrogen containing gas) or partially reduced and nitrided (by the ammonia containing gas). It remains homogeneous after reduction, if any, and the reduction conditions must be adjusted so that the atomic ratio Co/Al does not vary by more than 10% at the scale of 50 nm.

The homogeneous hydrated precipitate (amorphous or crystallized) thoroughly dealkalinized by washing, dried so as to reduce its content of volatile materials to less than 35% by weight and then thermally activated at a temperature from 250° to 600° C. for at least 0.5 hour, may be finally alkalinized as follows: the homogeneous product resulting from the thermal activation is crushed so as to obtain a powder with a particle size of at most 0.2 mm, then the alkalinizing agent (at least one A metal) is added, for example by mixing said product with an aqueous and/or organic solution containing at least one compound of at least one A metal in the above mentioned proportions.

After the addition of the alkalinizing agent, the paste may optionally be shaped by extrusion (thus giving, after drying and activation, extrudates having good mechanical properties), then it is dried by any known technique. After drying it may be advantageous to effect a maturation in surrounding air during a sufficient time to reduce the water content of the product to less than 25% and preferably less than 20% by weight.

Another way of adding the alkalinizing agent with a simultaneous shaping consists of placing the above mentioned powder in a bowl granulation turbine and then to spray over the powder, driven in rotation, the aqueous or organic solution containing the alkalinizing agent.

By this way calibrated balls (e.g. of a 2.4 to 5 mm diameter) are obtained, which, after optional maturation, drying and thermal activation lead to a homogeneous activated catalyst having good mechanical properties.

During the step of impregnating the dried product or the thermally activated product with at least one compound of a metal A, it may be advantageous to further add at least one soluble compound of at least one other metal selected from the group consisting of aluminum, zinc, chromium, M metals and N metals. The metals in the form of anionic complexes (aluminate, zincate, chromate, chromite, manganate, permanganate, perrhenate, oxalato, ferrate, citrate, malate etc ...) are particularly convenient for this mode of operation of the present process.

Another process whereby the alkalinization operation can be combined with the shaping operation consists of making a suspension containing the activated catalyst in a proportion of about 30-80% by weight and at least one metal A, and of effecting a flast roasting in an atomizer operating in the presence of a combustion gas containing less than 1 mg of sulfur per N.M$^3$ and whose temperature at the input is at least 500° C. Microspheres of 10-700 μm are thus obtained. They can be used in a liquid phase process with catalyst circulation.

The alkalinized catalyst, prepared as above stated (homogeneous paste, homogeneous extrudates, homogeneous balls, homogeneous microspheres) optionally matured, dried if necessary so as to bring its content of volatile materials to less than 35% by weight and, preferably, less than 25% by weight, is finally thermally activated in the above-mentioned conditions and in the presence of the above-mentioned gaseous reactants.

However this second thermal activation will be preferably conducted between about 350° and about 550° C. for a sufficient time to reduce the volatile material content of the product to less than 12% by weight.

When the alkalinized and then thermally activated catalyst has not been shaped in the above mentioned conditions, it will be shaped as follows:

The homogeneous product, thermally activated is crushed, for example to particles of less than 0.5 mm, admixed in a proportion of 0.5-5% of its weight with at least one pelletizing adjuvant compound selected from the group formed of graphite, stearic acid, stearates, and optionally a porosity adjuvant selected from cellulose and powders of vegetal origin containing the same, nitrates and ammonium carbonates, combustible fabric fibers, naphthalene, and finally pelletized to solid cylinders of 3-6 mm diameter or to toric cylinders of 3-6 mm external diameter, 1-4 mm internal diameter and 2-6 mm height.

The catalysts shaped as pellets will be optionally subjected to a final thermal activation in the above stated operating conditions.

The thermally activated catalyst, ready for use, consists of a very homogeneous association of oxides (optionally some of them may be reduced at least partly, inasmuch as a thermal activation has been conducted in a generally reducing medium). In this very homogeneous association of oxides, the metals, and particularly cobalt and aluminum are distributed very homogeneously on a 5 nm scale, and the relative variations of the atomic ratio Co/Al are lower than 15% and preferably lower than 10%. The specific surface of said catalysts varies form about 20 to about 300 m$^2$g$^{-1}$. The thermal activation, when conducted in the presence of at least one alkali and/or alkaline-earth metal A, and at a temperature of at least 350° C., may result in the recrystallization of specified particles of cupric oxide CuO (tenorite) visible in X-ray diffraction, without modifying the cobalt dispersion with respect to aluminum and metal A and according to the case; with respect to the other optional metals (Zn, Cr, M, N).

The operating conditions of use of these catalysts for manufacturing alcohols are usually as follows:

The catalyst, introduced into the reactor, is in a first step prereduced by a mixture of an inert gas (nitrogen for example) with at least one reducing compound selected from the group formed of hydrogen, carbon monoxide, alcohols and $C_1$ and $C_2$ aldehydes, the molar ratio of the reducing compound to the mixture of reducing compound with inert gas ranging from 0.001:1 to 1:1.

The prereduction temperature generally varies from 100° to 750° C., preferably from 150° to 550° C., the total pressure being usually from 0.1 to 10 MPa and preferably from 0.1 to 6 MPa; the hourly volume rate is usually from $10^2$ to $4.10^4$ hour$^{-1}$ and preferably from $5.10^2$ to $10^4$ hour$^{-1}$.

After a first reduction phase, conducted for example between about 150° and about 250° C., in the presence of the above mentioned reducing mixture and with a molar ratio reducing gas/reducing gas+inert gas from 0.001 to 0.1 and preferentially from 0.005 to 0.05, for a sufficient time to obtain equal concentrations of reducing gas at the input and at the output of the reactor (i.e. until the first reduction step is ended), it may be advantageous, in a second phase, to increase the temperature and optionally to increase also the concentration of reducing gas, and to continue the reduction under more severe conditions:

The reduction temperature is then selected from about 220° C. to about 750° C. and, preferentially from about 240° to about 550° C., the molar ratio reducing gas/reducing gas+inert gas is then comprised between 0.01 and 1 and, preferentially, between 0.05 and 1, the pressure and hourly volume rate being kept inside the above mentioned ranges.

The prereduction of the catalyst will be preferentially conducted in gaseous phase, even when, subsequently, the reaction of alcohols synthesis is conducted in liquid phase.

The proper alcohols synthesis reaction is effected in the following operating conditions: the pressure is usually between 2 and 25 MPa and preferably between 5 and 15 MPa, the molar ratio $H_2/CO+CO_2$ is advantageously between 0.4 and 10, but preferably between 0.5 and 4, and the temperature is from 200° to 400° C., preferably from 240° to 350° C.

The hurly volume rate (expressed as NTP volume of the gas mixture per volume of catalyst and per hour) is usually comprised between 1,500 and 60,000 $h^{-1}$ and preferably between 2,000 and 20,000 $h^{-1}$.

The catalyst may be used as calibrated fine powder (10–700 μm) or as particles of an equivalent diameter of 2 to 10 mm, in the presence of a gas phase or a liquid phase (under the operating conditions) together with a gas phase. The liquid phase may consist of one or more alcohols and/or hydrocarbons having at least 5 and preferably at least 10 carbon atoms.

According to this operating mode the superficial velocities of the gas and the liquid, under the temperature and pressure conditions the process, are of at least 1–5 cm/sec and preferably at least 3 cm/sec. By superficial velocity is meant the ratio of the flow rate by volume to the reaction cross-sectional area considered as empty.

The following examples describe different embodiments of the invention but are not intended to limit in any way the scope of the invention.

EXAMPLES NO. 1 TO 18

The manufacture of catalysts A to N whose properties are given in Tables II and VII is first described; the details of manufacture are given in Tables III to VI.B.

The manufacture of the catalysts A, M, N and P is described in detail hereinafter, that of the other catalysts is only summarized in the above Tables.

CATALYST A 241.6 g of copper nitrate trihydrate (1 g.at. Cu), 145.52 g cobalt nitrate hexahydrate (05 g.at. Co), 225.10 g of aluminum nitrate hexahydrate (0.6 g.at. Al) and 148.75 g zinc nitrate hexahydrate (0.5 g.at.Zn) are dissolved in 3 l of water. The solution (solution A, 0.43 g.at./l) is diluted to 6 liters and heated to 70° C.

540 g of di-sodium carbonate are separately dissolved into water heated to 70° C. (solution B, 1.27 g.at. Na/l), the final volume being 8 liters.

The solutions A and B are simultaneously added in 2 hours to a 25 liter heated reactor containing 5 l of alkalinized water of pH 8 at 70° C., the feed rates being adapted to maintain the pH between 6.90 and 7.10. The resultant precipitate, after 3 washings with 15 l water, contains 30%. b.w. of non-alkaline metal oxides and 0.05% b.w. of sodium with respect to the oxides. It is crystalline, its X-ray diffraction diagram has been indexed and the results are given in Table I. 724 g of precipitate are contacted with 2.3 l of a solution comprising 22 g of 100% pure di-potassium carbonate. After 30 mn of intense stirring, the precipitate is filtered again, dried in a ventilated oven for 16 hours at 80° C., then 3 hours at 100° C. (it then comprises 71% of oxides) and activated for 4 hours at 400° C. in the air. The volatile matter content is then 3.8%. The powder obtained by crushing to particles of less than 0.5 mm is admixed with 1% b.w. of magnesium stearate, pelletized and activated for 3 hours at 350° C. in the air. 170 g of catalyst is obtained; its specific surface is 120 m²/g.

CATALYST M 1.25 mole of aluminum nitrate nonahydrate (469 g), 0.1 mole of zirconium nitrate pentahydrate (43 g), 0.2 mole of zinc nitrate hexahydrate (60 g) and 1.6 moles of citric acid monohydrate are dissolved in 2 liters of water at 80° C. 0.8 mole of copper as basic copper carbonate of 55.3% Cu content (92 g) and 0.7 mole of cobalt carbonate 2 Co $CO_3$, Co(OH)$_2$, H$_2$O of 33.06% cobalt content (124.8 g) are added slowly and heating is continued up to complete dissolution of the products.

The solution is evaporated in a rotary evaporator up to formation of a viscous solution (viscosity: 1.5 Pa.s) which is dried at 80° C. for 24 hours in a vacuum stove. The resultant homogeneous vitreous material obtained is calcined at 400° C. in a rotary oven at a rate of 100 g/h. The residence time is 3 hours.

230 g of the resultant product, corresponding to 210.5 g of oxides, are mixed for 30 mn with 250 ml of a solution containing 15.4 g of 100% pure sodium hydroxide and 2.74 g of ammonium perrhenate (1.9 g Re) in a HOBBART mixer. The resultant homogeneous paste is placed on plates, aged in ambient air for 10 h, dried in a stove at 110° C. (16 h) and then calcined in a rotary oven at 400° C. for 1 h.

The resultant mixed oxide is crushed to particles of less than 0.5 mm, admixed with 2% b.w. of natural graphite of 0.05% iron content, pelletized to hollow cylinders with an external diameter and a height of 5 mm and an internal diameter of 2.4 mm and calcined again in a static oven at 380° C. for 6 h. The filling density of the catalyst is 1.05 kg/l and its specific surface, determined by the B.E.T. method, 36 $m^2g^{-1}$.

CATALYST N

A catalyst as calibrated microballs is prepared.

The catalyst of example J, after calcination in the air at 435° C. for 16 h, is made alkaline and shaped as follows:

The following suspension is prepared:
1780 g of a homogeneous oxide of the composition: $Cu_1Co_{0.5}Al_{0.95}Zn_{0.15}O_{3.07}$
137 g of di-sodium carbonate $Na_2 CO_3$
10 g of methocel (R)
1800 g of water.

The suspension is atomized in an apparatus under the following conditions:
input temperature: 700° C.
output temperature: 250° C.
air feed rate: 200 m³/hour
solid feed rate: 10 kg/hour 1480 g of homogeneous catalyst are obtained. Its composition is: $Cu_1Co_{0.5}Al_{0.95}Zn_{0.15}Na_{0.26}O_{3.20}$ as cenospheres having a particle size of 7–15 nm and a filling density of 0.88 $g.ml^{-1}$. The specific surface is 132 $m^2g^{-1}$.

CATALYST P

This catalyst of atomic composition $Cu_{0.5}Co_{0.35}Al_{1.2}Zn_{0.5}Ca_{0.2}Mg_{0.4}Li_{0.34}$ is prepared by continuous precipitation in the conditions described for catalyst C.

The solution A containing the metals Cu, Co, Al, Zn, Ca and Mg, having a 0.46M metal concentration is made to precipitate at 80° C. with di-sodium carbonate (0.93N of $Na^+$). The precipitate is aged in batch at 70° C. for 150 mn and washed in the hot; it contains, after washing, 0.02% of Na and 23% of oxides; the precipitate is dried in an air stream at 60° C. for 10 h and 120° C. for 3 h, and then thermally activated at 400° C. for 3 h. 410 g of the calicined product, containing 390 g of oxides, are mixed with 16.3 g of lithium hydroxide dissolved in 740 ml of solution. The resultant paste is dried by atomization and then thermally activated at 350° C. for 4 h. After crushing, addition of graphite, pelletizing (filling density of the pelletized product: 1.3 kg/l) and thermal reactivation (350° C., 2 h), 401 g of catalyst are obtained.

CATALYST Q

This catalyst, having the atomic composition $Cu_{0.8}Co_{0.3}Al_1Zn_{0.8}Na_{0.132}Li_{0.132}$, is prepared in the same manner as catalyst P. The alkalinisation is effected by mixing 420 g of the calcined product (404 g of oxide) with 950 ml of an aqueous solution of 27 g of lithium acetate dihydrate and 21.8 g of sodium acetate. The filling density, after pelletizing, is 1.0 kg/l.

Catalyst testing

The catalysts of examples A to M have been tested in a pilot unit operated continuously with 20 ml of catalyst.

The examples utilizing the catalysts No. 1 to 18 of Table VIII show the improved stability of said catalysts.

The following examples 19 and 20 illustrate the use of the catalysts in a liquid phase process.

The performances are defined as follows:

mass productivity to alcohols P: number of grams of alcohols obtained in one hour, expressed with respect to the weight (in grams) of the catalyst employed, selectivity b.w. to higher alcohols $C_2^+OH$: ratio by weight $100 \times$ weight of alcohols $C_2^+OH$/total weight of the formed alcohols, selectivity of the conversion of CO and $CO_2$ to alcohols ($S_A$): $C_1OH$, $C_2OH$, $C_3OH$, $C_4OH$ ... $C_nOH$ representing the number of gram molecules of each alcohol formed; it is reduced that $N_C = C_1OH + 2 \cdot C_2OH + 3 C_3OH + 4 C_4OH + \ldots + n C_n OH$ is the number of gram molecules of $(CO+CO_2)$ converted to alcohols.

The selectivity $S_A$ is thus expressed as:

$$S_A = 100 \frac{N_c}{\text{mol} \cdot \text{g (CO + CO}_2\text{) at the input} - \text{mol} \cdot \text{g (CO + CO}_2\text{) at the output}}$$

The by-products of the reaction are methane, $C_2^+$ hydrocarbons as well as certain oxygen compounds such as aldehydes, esters and ketones, present as traces.

EXAMPLE NO. 19

The reactor has a diameter of 2.5 cm and a useful height of 2 m; it contains 400 ml of the catalyst D (540 g) prereduced in gas phase in the conditions (a) of Table IX. The reactor is fed with 1.7 m³/h of synthesis gas having the composition stated in examples 1 to 13, thus $H_2/CO+CO_2=2$ (by mole) and $CO_2/CO+CO_2=0.14$ (by mole), under a pressure of 6 MPa, this gas being circulated downwardly (in down-flow), and with 42 l/h of a paraffinic $C_{10}-C_{16}$ hydrocarbon cut desulfurized to less than 2 ppm of sulfur, also circulated downwardly and which is thereafter recycled to the reactor.

It can be calculated that the superficial velocity of these materials (ratio of the volumic feed rate of the liquid and gas phases, in the conditions of temperature and pressure selected for the reaction, to the cross-section of the reactor considered as catalyst-free) is 3.2 cm·sec⁻¹ for the gas and 3.2 cm·sec⁻¹ for the liquid.

The hourly volumic velocity is 4250 h⁻¹.

The performances are the following:

| time | 100 h | 500 h | 1000 h | 2000 h |
|---|---|---|---|---|
| temperature (°C.) | 285 | 290 | 290 | 290 |
| productivity to alcohols by weight (P) in g/h/g of catalyst | 0.15 | 0.16 | 0.15 | 0.14 |
| selectivity b.w. to heavy alcohols (%) ($SC_2^+OH$) | 70.7 | 71 | 69.8 | 69.1 |
| including $C_2$ | 29.5 | 30 | 30.5 | 30.7 |
| $C_3$ | 14.5 | 14.0 | 13.6 | 13.4 |
| $C_4$ | 11.6 | 11.4 | 11.7 | 11.6 |
| $C_5^+$ | 15.1 | 15.6 | 14 | 13.4 |
| selectivity to alcohols ($S_A$) | 68 | 70 | 70 | 71 |

EXAMPLE NO. 20

The catalyst N, which has been prereduced in gas phase in the reactor under the conditions (b) of Table IX is used in the following conditions:

The reactor of example No. 14 is fed with 1.7 m³/h of synthesis gas of the composition $H_2/CO+CO_2=1.5$ and $CO_2/CO+CO_2=0.25$ under a pressure of 8 MPa, the gas being now circulated upwardly, and with 45 l/h of the hydrocarbon cut used in example 19 and containing 25% of catalyst N in suspension, also circulated upwardly. The space velocity of the liquid is 3.45 cm·sec⁻¹ and that of the gas 3.2 cm·sec.⁻¹.

It can be determined that the volumic hourly velocity is now 6900 h⁻¹.

The results are the following:

| time | 100 h | 500 h | 1000 h |
|---|---|---|---|
| temperature (°C.) | 275 | 280 | 280 |
| productivity b.w. to alcohols (P) | 0.18 | 0.19 | 0.18 |
| selectivity b.w. to heavy alcohols ($SC_2^+OH$) | 56.2 | 57 | 56.1 |
| $S_A$ (selectivity to alcohols) | 75 | 76 | 75.3 |

EXAMPLE NO. 21

300 g of the catalyst P are placed in an industrial monotube of 21 mm internal diameter and 2 m height; the tube is cooled externally with boiling water whose temperature (250° to 350° C.) is controlled by the pressure.

The catalyst is first prereduced with 4% hydrogen in nitrogen (5 h-stages respectively at 160°-180°-200°-220°-240° C.) and the reduction is terminated with pure hydrogen, for 3 h at 240° C., then 300° C., 400° C., 500° C., 550° C.

The test is conducted with a $H_2$—CO reaction mixture having a ratio $H_2/CO$ of 2 and containing 2% of $CO_2$; the unit is equipped with a liquid-gas separator and a recycle compressor for recycling of the unconverted gas; the ratio of the recycled gas to the adduct gas is from 4 to 5; the performances are as follows (total pressure: 80 bars):

| Hours of run | T° C. | Total conversion of CO | Production of alcohols by weight | Selectivity b.w. to higher alcohols | $S_A$ | COMPOSITION OF THE RESULTANT ALCOHOL PHASE | | |
|---|---|---|---|---|---|---|---|---|
| | | | | | | Alcohols | Hydrocarbons | Methyl esters |
| 100 | 290–310 | 95 | 0.105 | 45 | 73 | 98.4 | 0.5 | 1.1 |
| 1000 | 305–325 | 94 | 0.102 | 36 | 76 | 98.5 | 0.7 | 0.8 |
| 8000 | 315–335 | 93.5 | 0.100 | 34 | 75 | 98.6 | 0.6 | 0.9 |

EXAMPLE NO. 22

200 g of the catalyst Q are placed in the industrial mono-tube of example No. 21; the reduction conditions and the test conditions are those of example No. 21, although the operating pressure is now varied; the object of this example is to show the favorable effect of the operating pressure on the catalyst activity.

| Hours of run | Operating pressure | T° C. | Total conversion of CO | Production of alcohols b.w. | Selectivity b.w. to higher alcohols | $S_A$ |
|---|---|---|---|---|---|---|
| 500 | 80 | 300–320 | 92 | 0.105 | 39 | 74 |
| 550 | 160 | 300–335 | 94 | 0.195 | 36 | 76 |
| 590 | 240 | 290–340 | 96 | 0.280 | 32 | 78 |

The following examples show the advantageous effect of adding noble metals of group VIII on the performances of the catalysts which are the object of the present invention.

The manufacture of these catalysts is first described.

CATALYST $Q_1$ 100 g of the non-alkalinized catalyst Q are admixed with 120 ml of an alcoholic solution of 0.8 g palladium as acetate; after drying at 100° C. in an air stream and thermal activation at 350° C. for 2 h, the alkalinization is performed as for catalysts P and Q; 90 g of pellets are obtained, whose filling density amounts to 1.0 kg/l.

CATALYST $Q_2$

The same experiment is performed by replacing the 0.8 g of palladium with 0.4 g of rhodium as rhodium (III) acetylacetonate.

CATALYST $Q_3$

The same experiment is carried out with the 0.8 g of palladium of example $Q_1$ replaced with 0.2 g of palladium and 0.4 g of ruthenium as acetylacetonates in alcoholic solution.

EXAMPLES NO. 23, 23A, 23B, 23C

The catalysts Q, $Q_1$, $Q_2$, $Q_3$ are tested in the conditions of Table VIII; the catalyst is prereduced according to the method of example 21.

The performances determined after 500 h are described in Table X.

TABLE I

RHOMBOHEDRAL-PHASE OF THE HYDROXYCARBONATE TYPE HEXAGONAL MESH a = 0.305 nm c = 2.24 nm space group R-3M

| Miller index | d(nm) | i/io |
|---|---|---|
| 003 | 0.747 | 100 |
| 006 | 0.373 | 55 |
| 101 | 0.262 | 3 |
| 012 | 0.257 | 55 |
| 009 | 0.249 | 1 |
| 104 | 0.239 | 6 |
| 015 | 0.227 | 40 |
| 107 | 0.203 | 3 |
| 018 | 0.1925 | 30 |
| 0012 | 0.187 | 2 |
| 10$\overline{1}$0 | 0.1709 | 10 |
| 01$\overline{1}$1 | 0.1613 | 6 |
| 11$\overline{0}$ | 0.1525 | 10 |
| 113 | 0.1494 | 12 |
| 0015 | 0.1493 | |
| 10$\overline{1}$3 | 0.1443 | 5 |
| 11$\overline{6}$ | 0.1412 | 6 |
| 01$\overline{1}$4 | 0.1369 | 2 |
| 02$\overline{1}$ | 0.1318 | 1 |
| 202 | 0.1312 | 2 |

Registration conditions: Cu K 35 KV 35 mA
back monochromate (graphite)

TABLE II (the number of oxygen gram. atoms is given for indication)

| CATALYST | | Atomic ratios | | | | | | | |
|---|---|---|---|---|---|---|---|---|---|
| | | Cu/Co | Al/Co | Zn/Co | A/Co | M/Co | M/Al | N/Co | N/Al |
| A | $Cu_1Co_{0.5}Al_{0.6}Zn_{0.5}K_{0.05}O_{2.93}$ | 2 | 1.2 | 1 | 0.1 | — | — | — | — |
| B | $Cu_1Co_{0.4}Al_1Zn_{0.4}Na_{0.25}O_{3.43}$ | 2.5 | 2.5 | 1 | 0.42 | — | — | — | — |
| C | $Cu_{0.7}Co_{0.6}Al_{0.9}La_{0.3}Na_{0.17}Rb_{0.007}O_{3.19}$ | 1.17 | 1.5 | — | 0.295 | — | — | 0.5 | 0.33 |
| D | $Cu_{0.8}Co_{0.5}Al_{0.65}Na_{0.30}O_{2.45}$ | 1.6 | 1.3 | — | 0.61 | — | — | — | — |
| E | $Cu_{0.9}Co_{0.6}Al_1Zn_{0.2}V_{0.15}O_{3.70}Na_{0.25}$ | 1.5 | 1.67 | 0.33 | 0.42 | 0.25 | 0.15 | — | — |
| F | $Cu_1Co_{0.7}Al_{1.1}Zn_{0.6}Fe_{0.1}Pr_{0.2}Ba_{0.02}K_{0.034}O_{4.44}$ | 1.43 | 1.57 | 0.86 | 0.007 | 0.14 | 0.09 | 0.284 | 0.18 |
| G | $Cu_{0.9}Co_{0.6}Al_{1.2}Th_{0.4}O_{4.33}Na_{0.45}$ | 1.5 | 2.0 | — | 0.756 | — | — | 0.67 | 0.33 |
| H | $Cu_{0.7}Co_{0.7}Al_{1.35}La_{0.3}Mn_{0.15}Na_{0.182}K_{0.044}O_{4.21}$ | 1 | 1.93 | — | 0.323 | 0.215 | 0.11 | 0.43 | 0.22 |
| I | $Cu_{1.3}Co_{0.3}Al_{0.65}Pr_{0.4}Fe_{0.15}O_{3.47}K_{0.127}$ | 4.33 | 2.17 | — | 0.424 | 0.5 | 0.23 | 1.33 | 0.61 |
| J | $Cu_1Co_{0.5}Al_{0.95}Zn_{0.15}Na_{0.26}O_{3.20}$ | 2 | 1.9 | 0.3 | 0.52 | — | — | — | — |
| K | $Cu_1Co_{0.5}Al_{0.95}Cr_{0.15}Na_{0.26}O_{3.28}$ | 2 | 1.9 | — | 0.52 | 0.3* | 0.16* | — | — |
| L | $Cu_{1.7}Co_{0.85}Al_{1.5}Ce_{0.1}Nd_{0.1}Th_{0.1}K_{0.15}O_{5.4}$ | 2 | 1.76 | — | 0.175 | — | — | 0.35 | 0.2 |
| M | $Cu_{0.8}Co_{0.7}Al_{1.25}Zr_{0.1}Re_{0.01}Zn_{0.2}Na_{0.38}O_4$ | 1.14 | 1.78 | 0.286 | 0.55 | 0.014 | 0.008 | 0.14 | 0.08 |

TABLE II-continued

| | | | | | | | | | |
|---|---|---|---|---|---|---|---|---|---|
| P | $Cu_{0.5}Co_{0.35}Al_{1.20}Zn_{0.5}Ca_{0.2}Mg_{0.4}Li_{0.34}$ | 1.43 | 3.43 | 1.43 | 2.69 | — | — | — | — |
| Q | $Cu_{0.8}Co_{0.3}Al_1Zn_{0.8}Na_{0.132}Li_{0.132}$ | 2.67 | 3.33 | 2.67 | 0.88 | — | — | — | — |

*M is chromium in this case.

(the number of oxygen gram. atoms is given for indication)

| CATALYST | | % metal weight with respect to the total metal weight | | | | | | |
|---|---|---|---|---|---|---|---|---|
| | | Cu | Co | Al | Zn | A | M | N |
| A | $Cu_1Co_{0.5}Al_{0.6}Zn_{0.5}K_{0.05}O_{2.93}$ | 44.2 | 20.5 | 11.3 | 22.7 | 1.3 | — | — |
| B | $Cu_1Co_{0.4}Al_1Zn_{0.4}Na_{0.25}O_{3.43}$ | 43.5 | 16.15 | 18.5 | 17.9 | 3.95 | — | — |
| C | $Cu_{0.7}Co_{0.6}Al_{0.9}La_{0.3}Na_{0.17}Rb_{0.007}O_{3.19}$ | 29.6 | 23.5 | 16.15 | — | 3.05 | — | 27.7 |
| D | $Cu_{0.8}Co_{0.5}Al_{0.65}Na_{0.30}O_{2.45}$ | 48.4 | 28.05 | 16.7 | — | 6.85 | — | — |
| E | $Cu_{0.9}Co_{0.6}Al_1Zn_{0.2}V_{0.15}O_{3.70}Na_{0.25}$ | 39.2 | 24.2 | 18.5 | 9 | 3.9 | 5.2 | — |
| F | $Cu_1Co_{0.7}Al_{1.1}Zn_{0.6}Fe_{0.1}Pr_{0.2}Ba_{0.02}K_{0.034}O_{4.44}$ | 29.8 | 19.35 | 13.90 | 18.4 | 2.7 | 1.98 | 9.95 |
| G | $Cu_{0.9}Co_{0.6}Al_{1.2}Th_{0.4}O_{4.33}Na_{0.45}$ | 25.1 | 15.5 | 14.2 | — | 4.56 | — | 40.7 |
| H | $Cu_{0.7}Co_{0.7}Al_{1.35}La_{0.3}Mn_{0.15}Na_{0.182}K_{0.044}O_{4.21}$ | 24.9 | 23.2 | 20.5 | — | 3.3 | 4.6 | 23.4 |
| I | $Cu_{1.3}Co_{0.3}Al_{0.65}Pr_{0.4}Fe_{0.15}O_{3.47}K_{0.127}$ | 44.05 | 9.4 | 9.35 | — | 2.66 | 4.5 | 30.05 |
| J | $Cu_1Co_{0.5}Al_{0.95}Zn_{0.15}Na_{0.26}O_{3.20}$ | 47.3 | 21.9 | 19.1 | 7.3 | 4.43 | — | — |
| K | $Cu_1Co_{0.5}Al_{0.95}Cr_{0.15}Na_{0.26}O_{3.28}$ | 48 | 22.3 | 19.4 | — | 4.55 | 5.8 | — |
| L | $Cu_{1.7}Co_{0.85}Al_{1.5}Ce_{0.1}Nd_{0.1}Th_{0.1}K_{0.15}O_{5.4}$ | 42.1 | 19.5 | 15.8 | — | 2.26 | — | 20.3 |
| M | $Cu_{0.8}Co_{0.7}Al_{1.25}Zr_{0.1}Re_{0.01}Zn_{0.2}Na_{0.38}O_4$ | 32 | 26 | 21.3 | 8.25 | 5.55 | 1.2 | 5.75 |
| P | $Cu_{0.5}Co_{0.35}Al_{1.20}Zn_{0.5}Ca_{0.2}Mg_{0.4}Li_{0.34}$ | 15.6 | 10.15 | 30.1 | 20 | 8.51 | — | — |
| Q | $Cu_{0.8}Co_{0.3}Al_1Zn_{0.8}Na_{0.132}Li_{0.132}$ | 24.1 | 8.40 | 24.2 | 30.9 | 1.88 | — | — |

TABLE III

| CATALYST | A | B | C |
|---|---|---|---|
| Precipitation conditions | Reactor: 25 l<br>Reaction time: 2 hours.<br>70° C.; pH 7 ± 0.1<br>(Metals) = 0.43 M<br>(Na+) = 1.27 M | Reactor: 1.1 l<br>Reaction time: 5 minutes<br>20° C.; pH 7 ± 0.05<br>(Metals) = 1.10 M<br>(Na+) = 3.47 M | Reactor: 35 l<br>Reaction time: 150 minutes<br>77–85° C.; pH 7.10 ± 0.1<br>(the pH is raised to 7.6 at the beginning of the salt addition)<br>(Metals) = 0.38 M<br>(Na+) = 0.80 M |
| Washings | cold (20° C.) | cold (20° C.) | warm (50° C.) |
| % Oxides content of the precipitate | 30/Ct. | 15/Am. | 52/Ct. |
| % Na/oxides | 0.05 | 0.5 | 0.02 |
| Addition of the alkaline agent | aqueous $K_2CO_3$ on the wet precipitate with filtration | Aqueous $Na_2CO_3$ on the wet precipitate without filtration | NaOH (30%) $Na_2CO_3$ (70%) on the wet precipitate with filtration<br>Ageing in air at 25° C. for 48 h. |
| Drying | aerated oven<br>80° C., 16 h<br>100° C., 3 h | By atomization<br>Input gas T = 250° C.<br>Residence time: 5 sec. | Drying:<br>30° C., 5 h<br>60° C., 10 h<br>80° C., 3 h<br>aerated oven |
| Oxides content after drying | 71 | 69.2 | 71.3 |
| Thermal activation No. 1 | 400° C./4 h in air | 380° C./5 h in nitrogen | 400° C./3 h in air |
| % Volatile matter of the activated product | 3.8 | 7.6 | 4.7 |
| Shaping | Pelletizing (1% of magnesium stearate) | Pelletizing (2% of graphite + 5% of ammonium carbonate) | Pelletizing (2% of graphite + 2% of cellulose fibers) |
| Thermal activation No. 2 | 350° C./3 h in air | 400° C./4 h in nitrogen | 350° C./2 h in air |

N.B.:
Ct. = crystallized precipitate
Am. = amorphous precipitate
(Metals) and (Na, K) = the concentrations of metals are expressed as g.at. of metals per liter.

TABLE IV

| CATALYST | C | E | J |
|---|---|---|---|
| Precipitation | Reactor: 8 l<br>Reaction time: 3 minutes<br>80° C., pH = 6.95 ± 0.05<br>(metals) = 0.46 M<br>(Na+) = 0.93 M | Reactor: 1.1 l<br>Reaction time: 10 minutes<br>20° C., pH = 7.05 ± 0.02<br>(metals) = 1.5 M<br>(Na+) = 2.45 M<br>Precipitation of $Cu_{0.9}Co_{0.6}Al_1Zn_{0.2}O_{3.2}$ | Reactor: 2 l<br>Reaction time: 7 minutes<br>18° C., pH = 7.05 ± 0.05<br>(metals) = 1.3 M<br>(sodium) = 2.65 M |
| Ageing | in batch, 150 mm/70° C. | NO | NO |
| Washings | warm (50° C.) | cold (22° C.) | cold |
| % oxide content of the precipitate | 21/Ct. | 18.5/Am. | 16.7/Am. |
| Na/oxides | 0.08 | 0.6 | 0.5 |
| Dryings | in nitrogen<br>30° C./16 h<br>60° C./10 h<br>80° C./3 h | 50° C./4 h<br>80° C./16 h<br>100° C./3 h<br>(crystallization of the rhomboedric phase) | atomization<br>Input T: 250° C.<br>Output T: 150° C.<br>Residence time: 1.5 sec. |
| Oxide content after drying | 70.1 | 71.3 | 66.8 |
| Heat activation No. 1 | 420° C./10 h | 470° C./6 h | 435° C./10 h in air |

TABLE IV-continued

| CATALYST | C | E | J |
|---|---|---|---|
| Addition of the alkaline agent | nitrogen: 94%<br>$NH_3$: 3%<br>$H_2O$: 3%<br>Mixing: 1 h<br>1 part of oxides<br>0.8 part of NaOH + RbOH solution in 50% $C_2H_5OH$ in water | nitrogen: 50%<br>air: 50%<br>(and of vanadium) ammonium metavanadate (0.15) (0.15 $V^{5+}$) and sodium oxalate (0.25 $Na^+$) + oxalic acid (0.3 mol · g) in 0.9 part of solution per part of oxide | Mixing: 1 part of catalyst and 0.5 part of aqueous $Na_2CO_3$ solution-<br>extrusion: 5 mm diameter |
| Drying | Slow evaporation in air<br>(48 h) + 35° C./10 h | Ageing in air: 72 h/20-25° C.<br>90° C./6 h | Ageing in air<br>22° C./48 h<br>+40° C./16 h<br>60° C./2 h<br>100° C./3 h |
| Thermal activation No. 2<br>Shaping | 420° C./3 h nitrogen<br>Pelletizing (2% cellulose, 1% stearic acid) | 400° C./3 h nitrogen<br>Pelletizing (2% Mg stearate) | (extrudates) |
| Thermal activation No. 3 | 350° C./6 h nitrogen | 300° C./3 h nitrogen | 400° C./3 h nitrogen |

(Abbreviations: see Table III)

TABLE V

| CATALYST | H | K | L |
|---|---|---|---|
| Precipitation conditions | Reactor: 1.1 l<br>reaction time: 10 minutes<br>20° C. – pH = 7.2 ± 0.05<br>(metals) = 1.2 M<br>$Na^+ + K^+$) = 3.35 M<br>K/Na = 0.24 (at.)<br>Precipitation by an alkaline solution $NaHCO_3 + K_2CO_3 + Na_2CO_3$ | Reactor: 50 l<br>reaction time: 3 hours<br>70° C. – pH = 7.05 ± 0.1<br>(metals) = 0.8 M<br>($Na^+$) = 1.5 M | Precipitate I<br>$Th_{0.1}Al_{0.3}O_{0.65}$<br>reactor: 2 l<br>reaction time: 10 minutes<br>20° C. – pH = 6.5 ± 0.2<br>(metals) = 1 M<br>($Na^+$) = 1.8 M<br>amorphous hydrated phase<br>Precipitate II<br>$Cu_{1.7}Co_{0.85}Al_{1.2}Ce_{0.1}Nd_{0.1}O_{4.7}$<br>amorphous hydrated phase<br>reactor: 2 l<br>reaction time: 10 minutes<br>20° C. – pH = 7.0 ± 0.1<br>(metals) = 1 M<br>($Na^+$) = 1.8 M<br>The precipitate II is formed by the simultaneous supply of the precipitate I, of the nitrates of the precipitate II and of sodium carbonate. |
| Washing | Controlled, to leave<br>Na/metals = 2.36%<br>K/metals = 0.95% | in the cold | in the cold, after formation of the mixed precipitate (I + II) |
| % oxides content of the precipitate | 14.8/Am. | 28.7/Ct. | 22/16/Am.<br>Precipitate I prec. (I + II) |
| % NaOH/oxides | | 0.05 | 0.4 |
| Alkalinization | see above | aqueous $Na_2CO_3$ with filtration | aqueous $K_2CO_3$, without filtration |
| Drying | by atomization<br>input T: 350° C.<br>output T: 160° C.<br>residence time: 1 sec. | 80° C./16 h<br>100° C./4 h | by atomization<br>input T: 600° C.<br>output T: 250° C.<br>residence time: 0.5 sec. |
| % oxides content after drying | 77.3 | 70.5 | 85 |
| Thermal activation No. 1 | 400° C./3 h in nitrogen | 350° C./5 h in air | 450° C./4 h in an air stream |
| % volatile matter in the activated product | 6.1 | 7.6 | 5.9 |
| Shaping | pelletizing (2% graphite with 0.01% iron) | pelletizing (3% graphite with 0.01% iron) | Pelletizing (2% stearic acid and 3% cellulose AVICEL) |
| Thermal activation No. II | 420° C./2 h in nitrogen | 400° C./2 h | 400° C./2 h in air |

(Abbreviations: see Table III)

TABLE VI-A

| CATALYST | F | I | G |
|---|---|---|---|
| Precipitation conditions | Precipitate I:<br>$Pr_{0.2}Zn_{0.2}Al_{0.2}O_{0.8}$<br>Reactor: 25 l<br>Reaction time: 2 hours<br>75-80° C. - pH 6.7 ± 0.2<br>(metals) = 0.45 M<br>($NH_4^+$) = 0.95 M<br>(precipitation with ammonium carbonate) + ageing 3 h/70° C. | Precipitate I:<br>$Pr_{0.2}Fe_{0.15}O_{0.53}$<br>Reactor: 1.1 l<br>Reaction time: 5 minutes<br>20° C. - pH 6.5 ± 0.2<br>(metals) = 1.5 M<br>($Na^+$) = 3 M<br>(amorphous precipitate, 17% oxides) | Reactor: 1.1 l<br>Reaction time: 5 minutes<br>75-80° C., pH 7.1<br>(metals) = 0.5 M<br>($Na^+$) = 1.15 M |

TABLE VI-A-continued

| CATALYST | F | I | G |
|---|---|---|---|
| | (pH raised to 7.3) (crystallized precipitate - 22% oxides) Precipitate II: $Cu_1Co_{0.7}Al_{0.9}Zn_{0.4}Fe_{0.1}O_{3.6}$ Reactor: 2.1 l Reaction time: 25 minutes admixing of the washed precipitate I + nitrates II in a ratio 1Cu/0.2Pr + $Na_2CO_3$ solution 70–75° C. - pH 7.0 ± 0.1 (metals) = 0.45 M ($Na^+$) = 0.95 M | Precipitate II: $Cu_{1.3}Co_{0.3}Al_{0.65}Pr_{0.2}O_{2.87}$ Reactor: 35 l Reaction time: 3 hours 80° C. - pH 7.02 ± 0.05 (metals) = 0.3 M ($Na^+$) = 0.85 M admixing of the amorphous precipitate I + nitrates precipitate II in ratio 1.3Cu/0.15Fe + $Na_2CO_3$ solution. | |
| Ageing | in batch, 2 h at 70–75° C. (pH increased to 8.0) | NO | 60 mn 80° C. |
| Washing | in the cold | in the cold | in the cold |
| Oxides content of the precipitate | 23.5/Ct. | 35/Ct. | 25/Ct. |
| % Na/oxides | 0.09 | 0.12 | 0.06 |
| Dryings | 50° C./16 h 80° C./5 h 100° C./2 h | ambiant air/72 h 60° C./16 h 90° C./3 h | 100° C./16 h +110° C./3 h |
| % Oxides | 73.5 | 70.2 | 74.5 |
| Alkalinisation | hereafter | hereafter | mixing of the dried precipitate with aqueous NaOH (0.5 part per part of precipitate) ageing 48 h, air drying 16 h 45° C. |
| Thermal activation No. 1 | 400° C./8 h/air | 450° C./10 h/air | 450° C./5 h/nitrogen |

(Abbreviations: see Table III)

TABLE VI-B

| CATALYST | F | I | G |
|---|---|---|---|
| Volatile substance in the activated catalyst | 6.0 | 3.7 | 4.9 |
| Addition of alkaline agent | Agglomeration to balls: 2–5 mm barium acetate + potassium acetate. Aqueous solution pulverized in the turbine of the bowl granulator 0.4 part of solution per part of oxide. | Mixing: 30 minutes (KOH dissolved in ethanol - 2 parts of solution per part of oxide) | (made above) |
| Ageing | Ageing 72 h in the air 50° C./16 h 100° C./3 h ventilated oven | evaporation in the air (5 days) | (made above) |
| Thermal activation No. 2 | 400° C./4 h air | 350° C./5 h air | (made above) |
| Shaping | (balls - made above) | pelletizing: 2% graphite 1.5% tergal fibers (L = 2 mm max.) | pelletizing 2% stearic acid |
| Thermal activation No. 3 | NO | 400° C./2 h air | 350° C./3 h nitrogen. |

TABLE VII

| CATALYST | Filling density | Appearance | Specific surface | Extreme limits of the atomic Al/Co ratio (20 determinations/20 particles)-Scale 5 nm magnification from $2 \times 10^6$ to $5 \times 10^6$ |
|---|---|---|---|---|
| A | 1.1 | pellets ⌀ 4 h = 3.2 mm | 120 | 1.14–1.26 |
| B | 1.2 | pellets ⌀ 4 h = 3.2 mm | 165 | 2.35–2.62 |
| C | 0.9 | hollow pellets ⌀ 5 ⌀ 2.4 h = 4.5 mm | 83 | 1.44–1.60 |
| D | 1.35 | pellets ⌀ 5 h = 4 mm | 65 | 1.21–1.35 |
| E | 1.05 | pellets ⌀ 5 h = 4 mm | 94 | 1.60–1.72 |
| F[*] | 1.4 | pellets ⌀ 4 h = 4 mm | 185 | 1.20–1.32 (*) |
| G | 1.15 | pellets ⌀ 4 h = 4 mm | 152 | 1.85–2.06 |
| H | 1.25 | Pellets ⌀ 5 h = 4.5 mm | 215 | 1.86–2.04 |
| I[*] | 1.0 | balls 2.5–5 mm | 168 | 2.05–2.30 (*) |
| J | 1.10 | extrudates ⌀ 4.8 l = 3 to 6mm | 86 | 1.83–2.01 |
| K | 0.85 | hollow pellets ⌀ 5 ⌀ 2.5 mm h = 4 mm | 56 | 1.79–1.95 |
| L[*] | 1.25 | pellets ⌀ 5 mm h = 5 mm | 192 | 1.33–1.46 (*) |
| M | 1.05 | hollow pellets | 36 | 1.72–1.86 |

TABLE VII-continued

| CATALYST | Filling density | Appearance | Specific surface | Extreme limits of the atomic Al/Co ratio (20 determinations/20 particles)-Scale 5 nm magnification from $2 \times 10^6$ to $5 \times 10^6$ |
|---|---|---|---|---|
| N | 0.88 | ⌀ 5 ⌀ 2.5 mm<br>h = 4.6 mm<br>microballs<br>⌀ = 7-15 mm | 132 | 1.87-2.03 |

(*) — determined on the cobalt-containing elemental particles (precipitate II of examples F, I, L) of a 3-100 nm size after the final thermal activation.
NB: — ⌀ is the diameter in mm of the particles.

TABLE VIII

TEST CONDITIONS:
$H_2/CO + CO_2 = 2$; $CO_2/CO + CO_2 = 0.14$.
Total pressure: 6 megapascals (MPa); average temperature of the catalyst bed: 270-320° C.; catalyst amount: 20 ml; feed rate ($H_2 + CO + CO_2$) liters NTP/h and per liter of catalyst - VVH = 3000 h$^{-1}$

| EXAMPLE of use No. | CATALYST | Mode | T °C. | PRODUCTIVITY b.w. to alcohols P | SELECTIVITY b.w. to higher alcohols S.C$_2^+$OH | $S_A$ |
|---|---|---|---|---|---|---|
| | | | | PERFORMANCES at t = 100 h | | |
| 1 | A | (a) | 290 | 0.11 | 62.5 | 65 |
| 2 | | (e) | 200 | 0.13 | 61 | 66 |
| 3 | B | (a) | 280 | 0.10 | 49 | 09 |
| 4 | | (b) | 280 | 0.12 | 56 | 65 |
| 5 | C | (a) | 285 | 0.14 | 70.2 | 63 |
| 6 | D | (a) | 275 | 0.10 | 72.5 | 62 |
| 7 | | (b) | 275 | 0.12 | 06.3 | 65 |
| 8 | E | (a) | 285 | 0.13 | 58.9 | 67 |
| 9 | F | (a) | 262 | 0.15 | 65.8 | 64 |
| 10 | G | (e) | 270 | 0.12 | 61.9 | 67 |
| 11 | H | (a) | 256 | 0.14 | 73.8 | 64 |
| 12 | | (d) | 260 | 0.12 | 65.4 | 67 |
| 13 | I | (e) | 250 | 0.11 | 39.2 | 75 |
| 14 | J | (a) | 280 | 0.12 | 54.1 | 69 |
| 15 | | (c) | 280 | 0.11 | 60.0 | 66 |
| 16 | K | (a) | 300 | 0.11 | 49.3 | 68 |
| 17 | L | (a) | 255 | 0.13 | 66.6 | 65 |
| 18 | M | (a) | 285 | 0.105 | 60.8 | 70 |
| | | | | PERFORMANCES at t = 1000 h | | |
| 1 | A | (a) | 300 | 0.11 | 60.6 | 66 |
| 2 | | (e) | 300 | 0.12 | 59 | 68 |
| 3 | B | (a) | 285 | 0.09 | 48.8 | 70 |
| 4 | | (b) | 290 | 0.10 | 54 | 66 |
| 5 | C | (a) | 200 | 0.13 | 68.5 | 62 |
| 6 | D | (a) | 275 | 0.085 | 65.8 | 65 |
| 7 | | (b) | 275 | 0.10 | 63.2 | 67 |
| 8 | E | (a) | 290 | 0.125 | 59.6 | 66 |
| 9 | F | (a) | 265 | 0.135 | 66.2 | 64 |
| 10 | G | (e) | 275 | 0.11 | 61.9 | 68 |
| 11 | H | (a) | 260 | 0.13 | 65.8 | 69 |
| 12 | | (d) | 270 | 0.14 | 62.7 | 65 |
| 13 | I | (e) | 255 | 0.10 | 40.5 | 74 |
| 14 | J | (a) | 285 | 0.115 | 52.8 | 70 |
| 15 | | (c) | 285 | 0.105 | 58.6 | 67 |
| 16 | K | (a) | 310 | 0.095 | 46.8 | 66 |
| 17 | L | (a) | 260 | 0.12 | 67.5 | 68 |
| 18 | M | (a) | 290 | 0.10 | 60.2 | 69 |

(a) (b) (c) (d) (e) are the operating conditions of the prior reduction (see Table IX)
S.C$_2^+$OH and $S_A$: see hereinbefore.

TABLE IX

CONDITIONS OF CATALYSTS PREREDUCTION
(TESTS OF TABLE VIII)

Mode of reduction (a) 2% hydrogen in nitrogen;
hourly volumetric velocity = 1500 h$^{-1}$
10 h-steps respectively at 170-190-210-240° C.

(b) prereduction according to (a), then:
5% hydrogen in nitrogen
hourly volumetric velocity 2000 h$^{-1}$, 3 h at 240° C.
3 h at 300° C.

(c) 10% hydrogen in nitrogen
(other conditions unmodified) 2 h at 400° C.
2 h at 500° C.
prereduction according to (a)
of 5 h-steps respectively at 160-180-200-230-260° C.
then hourly volumetric velocity:1500 h$^{-1}$
5% hydrogen in nitrogen
step of 10 h at 260° C.
then reduction in 100% pure hydrogen
step of 5 h at 300° C.
the pressure is raised to 3 MPa
step of 10 h at 350° C.

(d) prereduction according to (a)
then reduction with 4% CO in nitrogen
volumetric hourly velocity:2000 h$^{-1}$
2 h at 260° C.
2 h at 290° C.
2 h at 340° C.
1 h at 400° C.
1 h at 500° C.

(e) prereduction according to (a), then reduction with methanol (4% in nitrogen) at a hourly volumetric velocity of 500 h$^{-1}$:5 h at 240° C.

TABLE IX-continued

CONDITIONS OF CATALYSTS PREREDUCTION (TESTS OF TABLE VIII)

Mode of reduction 10 h at 270° C.

N B: The reductions are effected at 1 atm, except when otherwise stated.

TABLE X

| Catalyst | Q | Q1 | Q2 | Q3 |
|---|---|---|---|---|
| Example | 23 | 23A | 23B | 23C |
| Temperature | 310 | 285 | 300 | 280 |
| Productivity b.w. to alcohols | 0.095 | 0.130 | 0.120 | 0.117 |
| Productivity b.w. to higher alcohols | 0.037 | 0.043 | 0.066 | 0.050 |
| Productivity to methanol | 0.058 | 0.087 | 0.054 | 0.067 |
| Selectivity b.w. to higher alcohols | 38.9 | 33.1 | 55.0 | 42.7 |
| $S_A$ | 72.5 | 78.1 | 69.3 | 74.0 |

What is claimed is:

1. In a process for manufacturing primary alcohols, comprising reacting carbon oxides, said oxides being $CO, CO_2$ or a mixture thereof, with hydrogen, in the presence of a multimetallic catalyst, the improvement wherein said catalyst comprises copper, cobalt, aluminum, and at least one alkali or alkaline-earth metal A selected the group consisting of lithium, sodium, potassium, rubidium, cesium, beryllium, magnesium, calcium, strontium, and barium, such that the atomic ratios of said metals are:
Cu/Co=0.1-5, Al/Co=0.7-4, metal A/Co=0.05-1.5; wherein the proportions by weight of each metal element with respect to the total metals weight are:
copper=10-65%
cobalt=5-50%
aluminum=5-40%
metal A=0.1-15%
and wherein the catalyst has a homogeneity such that the cobalt/aluminum atomic ratio varies less than 15% from the average value of said ratio, determined on a 5 nanometer scale.

2. A process according to claim 1, wherein said catalyst further comprises chromium, and where the atomic ratio of Cr/Al is 0.001-0.3.

3. A process according to claim 1, wherein the catalyst is subjected to prereduction before use, said prereduction of the catalyst being effected by contact with a mixture of an inert gas and at least one reducing compound, in a molar ratio of reducing gas/reducing gas+inert gas of 0.001:1 to 1:1, said reducing gas being selected from hydrogen, carbon monoxide and the $C_1$ and $C_2$ alcohols and aldehydes; wherein the prereduction is effected at a temperature of 100° to 750° C., a pressure of 0.1 to 10 MPa, and a space velocity of $10^2$ to $4 \times 10^4$.

4. A process according to claim 1, wherein the reaction of the carbon oxides with hydrogen is effected at a temperature of 200°-400° C., a pressure of 2 to 25 MPa, and a molar ratio $H_2/CO + CO_2$ of 0.4 to 10.

5. A process according to claim 1, wherein the reaction of the carbon oxides with hydrogen is effected in the presence of a liquid phase comprising one or more alcohols and/or hydrocarbons having at least 5 carbon atoms per molecule.

6. A process according to claim 1, wherein said catalyst further comprises 0.02 to 0.8% by weight of at least one noble metal of group VIII of the periodic classification of the elements.

7. The process according to claim 1, wherein the atomic ratios of the metals are:
Cu/CO=0.5-4.5, Al/Co=0.9-2.6, metals A/Co=0.05-1.5; the proportions by weight of each metal, with respect to the total metals weight, are:
copper=20-50%
cobalt=9-40%
aluminum=7-30%
metal A=0.2-10%;
wherein at least one metal A is selected from sodium, potassium, rubidium, magnesium, calcium and barium; and wherein the catalyst has a homogeneity such that the cobalt/aluminum atomic ratio does not vary by more than 10% on a 5 nanometer scale.

8. A process according to claim 1, wherein said catalyst further comprises at least one of the following additional catalytic components:
(a) zinc, in a proportion of 1-50% by weight of the total weight of catalytic metals, the atomic ratio Zn/Co being 0.1-2;
(b) at least one metal M, selected from manganese, vanadium, iron and rhenium, the metals being present in a proportion of 0.1-10% by weight of the total weight of catalytic metals, and the atomic ratio $\Sigma M/Al$ being 0.001-0.3;
(c) at least one metal N, selected from scandium, yttrium, thorium, zirconium, and the rare-earth metals of atomic numbers 57 to 71 inclusive, the metals N being present in a proportion corresponding to 5-50% by weight of the total weight of catalytic metals, and the atomic ratio $\Sigma N/Al$ being 0.05-1.5; or
(d) chromium, in a proportion of 0.1-10% by weight of the total weight of catalytic metals, the atomic ratio Cr/Al being 0.001-0.3.

9. A process according to claim 1, wherein said catalyst is produced by a process comprising the steps of:
(a) dissolving in water at least one soluble compound of each of copper, cobalt and aluminum, and, where said catalyst further comprises at least one of said additional catalytic components, a soluble compound of each said component, in the presence of at least one organic complexing agent, said agent being a hydroxyacid, a polyacid, an aminoacid or an aminoalcohol, the proportion of complexing agent being 0.5-2 gram-equivalents of carboxyl or amine groups per gram-equivalent of metals;
(b) evaporating the resultant solution produced in step (a), under reduced pressure, and dehydrating the resultant viscous solution to reduce the water content to less than 10% by weight, thereby producing a vitreous, homogeneous and amorphous material; and
(c) thermally activating the vitreous material from step (b), at a temperature of 300°-600° C., and adjusting the amount of said metal A by at least one of washing, contacting with a solution of a compound of said metal A, drying, and thermal activation.

10. A process according to claim 1 wherein said catalyst is produced by a process comprising the steps of:
(a) coprecipitating a solution of soluble salts of copper, cobalt, aluminum and metal A said solution having an aggregate concentration of at most 1 gram-atom of said catalytic metals per liter, the coprecipitation being effected with a solution of sodium and/or potassium and/or ammonium carbonate and/or hydrogenocarbonate and/or hydroxide, having an aggregate concentration of at most 2 gram-atoms of alkali metals and/or NH$_4$ per liter, the coprecipitation being effected at a pH of 7±1, at a temperature of at least 30° C., and with a residence time in the reaction medium of at least 2 minutes; thereby producing a coprecipitate, being a hydrated mixed hydroxycarbonate which is crystallized at least in part in a rhombohedral structure;

(b) washing the resultant hydrated mixed hydroxycarbonate from step (a), to reduce its alkali content, expressed as weight of alkali to weight of metals, to 0.01–5%; and (c) drying and thermally activating the washed hydrated material from step (b), and adjusting the amount of said metal A by at least one washing, contacting with a solution of a compound of said metal A, drying, and thermal activation.

11. A process according to claim 1 wherein said catalyst is produced by a process comprising the steps of:

(a) coprecipitating a solution of soluble salts of copper, cobalt aluminum, and metal A said solution having an aggregate concentration of at most 1 gram-atom of said catalytic metals per liter, the coprecipitation being effected with a solution of sodium and/or potassium and/or ammonium carbonate and/or hydrogenocarbonate and/or hydroxide, having an aggregate concentration of at most 2 gram-atoms of alkali metals and/or NH$_4^+$ per liter, the coprecipitation being effected at a pH of 7±1, at a temperature of 0°–30° C., and with a residence time in the reaction medium of at most 5 minutes; thereby producing a coprecipitate, being an amorphous hydrated mixed hydroxycarbonate;

(b) directly washing the resultant hydrated mixed hydroxycarbonate from step (a), to reduce its alkali content, expressed as weight of alkali to weight of metals, to 0.1–3%; and (c) drying and thermally activating the washed hydrated material from step (b), and adjusting the amount of said metal A by at least one washing, contacting with a solution of a compound of said metal A, drying and thermal activation.

12. A process according to claim 7, wherein said catalyst is produced by a process comprising the steps of:

(a) dissolving in water at least one soluble compound of each of copper, cobalt, aluminum, and metal A, in the presence of at least one organic complexing agent, said agent being a hydroxyacid, a polyacid, an aminoacid or an aminoalcohol, the proportion of complexing agent being 0.5–2 gram-equivalents of carboxyl or amine groups per gram-equivalent of metals;

(b) evaporating the resultant solution produced in step (a), under reduced pressure, and dehydrating the resultant viscous solution to reduce the water content to less than 10% by weight, thereby producing a vitreous, homogeneous and amorphous material; and (c) thermally activating the vitreous material from step (b), at a temperature of 300°–600° C., and adjusting the amount of said metal A by at least one washing, contacting with a solution of a compound of said metal A, drying, and thermal activation.

13. A process according to claim 8, wherein said catalyst is produced by a process comprising the steps of:

(a) dissolving in water at least one soluble compound of each of copper, cobalt aluminum and metal A, in the presence of at least one organic complexing agent, said agent being a hydroxyacid, a polyacid, an aminoacid or an aminoalcohol, the proportion of complexing agent being 0.5–2 gram-equivalents of carboxyl or amine groups per gram-equivalent of metals;

(b) evaporating the resultant solution produced in step (a), under reduced pressure, and dehydrating the resultant viscous solution to reduce the water content to less than 10% by weight, thereby producing a vitreous, homogeneous and amorphous material; and (c) thermally activating the vitreous material from step (b), at a temperature of 300°–600° C., and adjusting the amount of said metal A by at least one washing, contacting with a solution of a compound of said metal A, drying, and thermal activation.

14. A process according to claim 7, wherein said catalyst is produced by a process comprising the steps of:

(a) coprecipitating a solution of soluble salts of copper, cobalt aluminum and, metal A said solution having an aggregate concentration of at most 1 gram-atom of said catalytic metals per liter, the coprecipitation being effected with a solution of sodium and/or potassium and/or ammonium carbonate and/or hydrogenocarbonate and/or hydroxide, having an aggregate concentration of at most 2 gram-atoms of alkali metal and/or NH$_4$ per liter, the coprecipitation being effected at a pH of 7±1, at a temperature of at least 30° C., and with a residence time in the reaction medium of at least 2 minutes; thereby producing a coprecipitate, being a hydrated mixed hydroxycarbonate which is crystallized at least in part in a rhombohedral structure;

(b) washing the resultant hydrated mixed hydroxycarbonate from step (a), to reduce its alkali content, expressed as weight of alkali to weight of metals, to 0.01–5%; and (c) drying and thermally activating the washed hydrated material from step (b), and adjusting the amount of said metal A by at least one washing, contacting with a solution of a compound of said metal A, drying, and thermal activation.

15. A process according to claim 8, wherein said catalyst is produced by a process comprising the steps of:

(a) coprecipitating a solution of soluble salts of copper, cobalt aluminum and metal A, said solution having an aggregate concentration of at most 1 gram-atom of said catalytic metals per liter, the coprecipitation being effected with a solution of sodium and/or potassium and/or ammonium carbonate and/or hydrogenocarbonate and/or hydroxide, having an aggregate concentration of at most 2 gram-atoms of alkali metal and/or NH$_4$ per liter, the coprecipitation being effected at a pH of 7±1, at a temperature of at least 30° C., and with a residence time in the reaction medium of at least 2 minutes; thereby producing a coprecipitate, being a hydrated mixed hydroxycarbonate which is crystallized at least in part in a rhombohedral structure;

(b) washing the resultant hydrated mixed hydroxycarbonate from step (a), to reduce its alkali content, expressed as weight of alkali to weight of metals, to 0.01–5%; and (c) drying and thermally activating the washed hydrated material from step (b), and adjusting the amount of said metal A by at least one of washing, contacting with a solution of a compound said metal A, drying, and thermal activation.

16. A process according to claim 7, wherein said catalyst is produced by a process comprising the steps of:

(a) coprecipitating a solution of soluble salts of copper, cobalt aluminum and metal A, said solution having an aggregate concentration of at most 1 gram-atom of said catalytic metals per liter, the coprecipitation being effected with a solution of sodium and/or potassium and/or ammonium carbonate and/or hydrogenocarbonate and/or hydroxide, having an aggregate concentration of at most 2 gram-atoms of alkali metals and/or $NH_4+$ per liter, the coprecipitation being effected at a pH of 7±1, at a temperature of 0°–30° C., and with a residence time in the reaction medium of at most 5 minutes; thereby producing a coprecipitate, being an amorphous hydrated mixed hydroxycarbonate;

(b) directly washing the resultant hydrated mixed hydroxycarbonate from step (a), to reduce its alkali content, expressed as weight of alkali to weight of metals, to 0.1–3%; and (c) drying and thermally activating the washed hydrated material from step (b), and adjusting the amount of said metal A by at least one washing, contacting with a solution of a compound of said metal A, drying, and thermal activation.

17. A process according to claim 7, wherein said catalyst is produced by a process comprising the steps of:

(a) coprecipitating a solution of soluble salts of copper, cobalt and aluminum and metal A, said solution having an aggregate concentration of at most 1 gram-atom of said catalytic metals per liter, the coprecipitation being effected with a solution of sodium and/or potassium and/or ammonium carbonate and/or hydrogenocarbonate and/or hydroxide, having an aggregate concentration of at most 2 gram-atoms of alkali metals and/or $NH_4+$ per liter, the coprecipitation being effected at a pH of 7±1, at a temperature of 0°–30° C., and with a residence time in the reaction medium of at most 5 minutes; thereby producing a coprecipitate, being an amorphous hydrated mixed hydroxycarbonate;

(b) directly washing the resultant hydrated mixed hydroxycarbonate from step (a), to reduce its alkali content, expressed as weight of alkali to weight of metals, to 0.1–3%; and (c) drying and thermally activating the washed hydrated material from step (b), and adjusting the amount of said metal A by at least one washing, contacting with a solution of a compound of said metal A, drying, and thermal activation.

* * * * *

UNITED STATES PATENT AND TRADEMARK OFFICE
CERTIFICATE OF CORRECTION

PATENT NO. : 4,659,742

DATED : 4-21-87

INVENTOR(S) : Philippe Courty et al

It is certified that error appears in the above-identified patent and that said Letters Patent is hereby corrected as shown below:

Column 26, Claim 9, Line 61:

reads: "justing the amount of said metal A by at least one of"
  should read: --justing the amount of said metal A by at least one--

Column 27, Claim 11, Line 25:

reads: "per, cobalt aluminum, and metal A said solution"
  should read: --per, cobalt, aluminum and metal A, said solution--

Column 28, Claim 13, Line 5:

reads: "of each of copper, cobalt aluminum and metal A, in"
  should read: --of each of copper, cobalt, aluminum and metal A, in--

Column 28, Claim 14, Line 27:

reads: "per, cobalt aluminum and, metal A said solution"
  should read: --per, cobalt, aluminum and metal A, said solution--

Column 28, Claim 15, Line 54:

reads: "per, cobalt aluminum and metal A, said solution"
  should read: --per, cobalt, aluminum and metal A, said solution--

UNITED STATES PATENT AND TRADEMARK OFFICE
CERTIFICATE OF CORRECTION

PATENT NO. : 4,659,742

DATED : 4-21-87

INVENTOR(S) : Philippe Courty et al

It is certified that error appears in the above-identified patent and that said Letters Patent is hereby corrected as shown below:

Column 26, Claim 10, Line 67:

reads: "per, cobalt, aluminum and metal A said solution"
 should read: --per, cobalt, aluminum and metal A, said solution--

Column 29, Claim 15, Line 7:

reads: "amount of said metal A by at least one of washing"
 should read: --amount of said metal A by at least one washing--

Column 29, Claim 16, Line 14:

reads: "per, cobalt aluminum and metal A, said solution"
 should read: --per, cobalt, aluminum and metal A, said solution--

Column 30, Claim 17, Line 10:

reads: "per, cobalt and aluminum and metal A, said solu-"
 should read: --per, cobalt, aluminum and metal A, said solu- --

Signed and Sealed this

Eighteenth Day of August, 1987

Attest:

DONALD J. QUIGG

*Attesting Officer*      *Commissioner of Patents and Trademarks*